United States Patent [19]
Drake

[11] 3,985,786
[45] Oct. 12, 1976

[54] PREPARATION OF UNSATURATED NITRILES
[75] Inventor: Charles A. Drake, Nowata, Okla.
[73] Assignee: Phillips Petroleum Company, Bartlesville, Okla.
[22] Filed: July 28, 1975
[21] Appl. No.: 599,735

[52] U.S. Cl. .................. 260/465.8 R; 260/464; 260/465 H; 260/465 K; 260/465.9
[51] Int. Cl.² ................................ C07C 120/00
[58] Field of Search .............. 260/465.8 R, 465.9, 260/465 H, 464

[56] References Cited
UNITED STATES PATENTS

| | | | |
|---|---|---|---|
| 2,280,058 | 4/1942 | Bruson | 260/465 H X |
| 2,394,962 | 2/1946 | Bruson | 260/465.8 R X |
| 2,460,536 | 2/1949 | Rogers | 260/465.9 X |
| 2,641,607 | 6/1953 | Albisetti, Jr. et al. | 260/464.9 X |
| 3,539,615 | 11/1970 | Plorde | 260/464 |
| 3,840,583 | 10/1974 | Turk et al. | 260/465.8 R |

OTHER PUBLICATIONS

Albisetti, et al.; J.A.C.S., 78 (1956) pp. 2637–2641.

Primary Examiner—Joseph Paul Brust

[57] ABSTRACT

An olefinically unsaturated nitrile, an olefinic hydrocarbon containing an allylic hydrogen and a monoadduct reaction product of an olefinic hydrocarbon and an olefinically unsaturated nitrile are contacted in the presence of water to produce unsaturated dinitriles.

20 Claims, No Drawings

PREPARATION OF UNSATURATED NITRILES

This invention relates to the production of unsaturated dinitriles. In a specific aspect of the invention relates to a reaction of an olefinically unsaturated nitrile, an olefinic hydrocarbon and a monoadduct of an olefinic hydrocarbon and an olefinically unsaturated nitrile in the presence of water to yield olefinically unsaturated dinitrile products having a greater number of carbon atoms than the unsaturated nitrile reactant.

In U.S. Pat. No. 2,641,607 (issued June 9, 1953), Albisetti et al describe the thermal reaction of a 2-alkenenitrile (e.g. acrylonitrile) with a neutral olefinic compound (e.g. isobutylene) in a first stage reaction to produce unsaturated mononitriles having a greater number of carbon atoms (e.g. 5-methyl-5-hexenenitrile). Albisetti et al state that the reaction effluent can be distilled to recover the unsaturated mononitrile product, and that the recovered unsaturated mononitrile product can be thermally reacted with a neutral olefinic compound in a second stage reaction to produce unsaturated dinitriles. The patentees state that the first stage reaction can be conducted in the presence or absence of an inert diluent or solvent. The patent lists hydrocarbons, ethers and esters as suitable inert organic solvents, and then states that the reaction also takes place in the presence of water as a diluent, the water serving as a heat transfer medium.

In *J. Am. Chem. Soc.* 78, pp 2637–2641 (1956), Albisetti et al describe further work with the thermal reaction of a 2-alkenenitrile with a neutral olefinic compound in a first stage and the subsequent reaction in a second stage of a neutral olefinic compound with the reaction product of the first stage to produce unsaturated dinitriles. The authors state that water can be employed as the reaction medium in the second stage reaction of acrylonitrile with 5-methyl-5-hexenenitrile to produce 5-methylenenonanedinitrile. The authors also state that in the case of polymerizable nitriles, the use of water as the medium prevented formation of tars.

In U.S. Pat. No. 3,840,583 (issued Oct. 8, 1974) Turk et al disclose that the yield of unsaturated dinitriles can be increased by contacting an unsaturated mononitrile, an olefin and a monoadduct reaction product of an unsaturated mononitrile and an olefin, wherein the monoadduct reaction product is present in significant amount during substantially the entire reaction period. The patentees stated that this single stage reaction could be carried out in the presence or absence of a solvent or diluent which is nonreactive with either the reactants or the reaction products. The patentees list various hydrocarbons, various ethers, tetrahydrofuran, dioxane, carbon tetrachloride and methylene chloride as representative commercially available nonreactive solvents that can be employed.

It has now been discovered that the utilization of an aqueous medium as the diluent in the Turk et al single stage process provides a greater increase in yield of unsaturated dinitriles than would be expected from the summation of the increase in yield in unsaturated dinitriles achieved by the utilization of water as the diluent in both stages of the Albisetti et al process and the increase in yield in unsaturated dinitriles achieved by the utilization of the Turk et al single stage reaction instead of the Albisetti et al two stage process.

Accordingly, it is an object of this invention to provide an improved process for the reaction of an olefinic hydrocarbon and an olefinically unsaturated nitrile in order to obtain an olefinically unsaturated dinitrile reaction product having a greater number of carbon atoms than the original nitrile. Another object is to provide an improved process which results in increased yields of high carbon number olefinically unsaturated dinitrile reaction products. Another object of the invention is to increase the percentage conversion of the reactants. A further object of the invention is to increase the selectivity of the reaction for the desired products. Yet another object of the invention is to increase the ratio of the desired products to undesired heavy byproducts. Other objects, aspects and advantages of the invention will be apparent from a study of the specification and the appended claims to the invention.

Any unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, nonconjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

$$RCH = CR - CN$$

wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, such as alkylcycloalkyl, cycloalkylalkyl, aralkyl and arylcycloalkyl radicals. Examples of unsaturated nitriles meeting the requirements of the above formula are acrylonitrile, methacrylonitrile, 2-decenenitrile, 3-cyclohexl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2nonenenitrile, and the like, and mixtures thereof.

Any acyclic or cyclic olefinic hydrocarbon compound can be employed in the practice of this invention, provided that the compound has at least one olefinic linkage having joined to one of the doubly bonded carbons a carbon atom having at least one hydrogen atom attached thereto, said doubly bonded carbon atoms being free of cyano groups attached thereto. The olefinic hydrocarbons preferably are free of acetylenic unsaturation and have from 3 to 18 carbon atoms per molecule with from 1 to 2 ethylenically unsaturated, nonconjugated double bonds as the sole aliphatic unsaturation. The preferred types of these compounds are the open chain monoolefinic hydrocarbons represented by the formula $R'_2C=CR'—CHR'_2$, wherein each R' is independently selected from the group consisting of hydrogen and hydrocarbyl radicals, said hydrocarbyl radicals being selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1phenyl-2-propene, and the like, and mixtures thereof.

Suitable monoadduct reactants include any monoadduct reaction product of an olefinic hydrocarbon, as hereinabove defined, and an unsaturated mononitrile, as hereinabove defined. It is believed that the olefinic hydrocarbon compound and the unsaturated mononitrile react in accordance with the "ene" reaction to produce, as the principal monoadduct reaction product, a compound having the structural formula

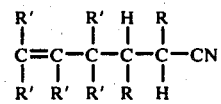

Generally, a lesser amount of an isomeric monoadduct reaction product having the formula

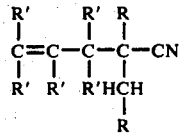

is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the ene reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4trimethyl-1-pentene is reacted with acrylonitrile the major monoadduct reaction products expected according to the "ene" reaction would be 5-methylene-7,7-dimethyloctanenitrile and 4-methylene-2,6,6-trimethylheptanenitrile with lesser amounts of 5,7,7-trimethyl-5-octenenitrile and 4,t-butyl-5-methyl-5-hexenenitrile. Other factors not fully understood at present may influence the relative amounts of the possible isomers in the monoadduct reaction product and in other instances presently employed analytical methods may not distinguish the various isomers present. Indeed, the monoadduct reaction product finds utility in many applications with no need of a costly separation of the isomers present in the monoadduct reaction product. The isomeric mixture reaction product produced by the reaction of an olefinic hydrocarbon and an definically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2(n-butyl)-4-pentenenitrile, 2-(n-butyl)-5-phenyl-4-pentenenitrile, and mixtures thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture consisting of the major isomer species 5-methylenenonanedinitrile and 5-methyl-4-nonenedinitrile, that contains minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the practice of this invention. In general the mol ratio of olefinically unsaturated mononitrile reactant to olefinic hydrocarbon reactant will be in the range of about 10:1 to about 0.1:1, preferably in the range of about 5:1 to about 0.2:1, and more preferably in the range of about 2:1 to about 0.3:1. In general the monoadduct reaction product will be employed in an amount such that during substantially the entire reaction period the net monoadduct reaction product present in the reaction mixture will constitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction of the olefinic hydrocarbon reactant and the olefinically unsaturated mononitrile reactant in the reaction zone less the monoadduct reaction product consumed by reaction with the olefinicaly unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinicaly unsaturated mononitrile reactant in the reaction zone, but it will be generally preferred for them to be the same. The total reaction mixture includes all fluid materials present in the reaction zone, i.e. reactants, diluents, products, byproducts, etc.

Any suitable reaction conditions for either a batch process or a continuous process can be employed in the practice of the invention. The reaction time employed in the practice of this invention can vary widely. Generally a time period of from about two minutes to about 48 hours, preferably from about 30 minutes to about 10 hours, and more preferably from about 1 hour to about 5 hours is an adequate period of time for olefin, unsaturated mononitrile and a monoadduct reaction product to be suitably admixed in the preparation of reaction products in high yields in a batch process. In a continuous process the liquid hourly space velocity will generally be in the range of about 0.05 to about 20, preferably in the range of about 0.1 to about 10, more preferably in the range of about 0.5 to about 2.

The reaction temperatures that can be employed in the practice of the invention can vary widely. Generally, however, suitable reaction temperatures are within the range of from about 100° C to about 500° C, and preferred reaction temperatures are within the range of from about 200° C to about 350° C.

The reaction pressures suited to the practice of this invention also vary widely. Reaction pressures within a range of from about atmospheric pressure to about 100,000 psig can be employed; however, reaction pressures within the range of from about 500 psig to about 4000 psig are preferably employed.

If desired, the processes of this invention can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an amount of from about 0.001 to about 5, preferably from about 0.1 to about 1, percent by weight inhibitor based on the weight of unsaturated mononitrile reactant be employed. Suitable inhibitors include hydroquinone, 2,6-di-tert-butyl-para-cresol, 2,6-di-tert-butylhydroquinone, 4-tert-butylcatechol, para-hydroxydiphenylamine, and the like, and combinations thereof.

The reaction of the above described olefinic hydrocarbon reactant, olefinically unsaturated mononitrile reactant and monoadduct reaction product reactant is carried out in the presence of an aqueous diluent, preferably comprising at least 50 weight percent water, more preferably at least 80 weight percent water, and more preferably consisting essentially of water. The codiluent, if employed, can be any solvent or diluent which is nonreactive with either the reactants or the reaction products. Examples of suitable codiluents include benzene, toluene, para-xylene, ortho-xylene, meta-xylene, ethylbenzene, diethyl ether, ethyl propyl ether, dibutyl ether, tetrahydrofuran, dioxane, cyclohexane, carbon tetrachloride, methylene chloride, and the like, and mixtures thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone. The amount of diluent currently preferred is in the range of about 0.1 to about 20 parts by weight of total diluent per part by weight of olefinically unsaturated mononitrile reactant charged to the reaction zone. The advantages of the aqueous diluent system include improved slectivity to the desired olefinically unsaturated nitrile and reduced amounts of heavy polymeric byproduct. This latter byproduct is particularly objectionable because it tends to foul reactor surfaces.

A convenient method of carrying out this invention comprises heating a mixture of an olefinically unsaturated mononitrile (e.g. acrylonitrile), an olefinic hydrocarbon compound (e.g. isobutylene), and a monoadduct reaction product reactant (e.g. a mixture of 5-methyl-5-hexenenitrile and 2,4-dimethyl-4-pentenenitrile) in a reaction pressure vessel at a temperature within the range of about 240° to about 350° C and at pressures of from about 500 to about 4000 psig, the mol ratio of the olefinically unsaturated mononitrile to the olefinic hydrocarbon being in the range of about 5:1 to about 0.2:1, and the concentration of the monoadduct reaction product reactant in the reaction mixture being in the range of about 20 to about 80 weight percent. Thereafter, the resulting olefinically unsaturated dinitrile reaction product is readily isolated from the reaction effluent mixture by any convenient product recovery method, such as fractional distillation. The reaction can be promoted indefinitely, in apparatus well known to the art and suited to either batch or continuous reaction conditions, until the mononitrile reactant and/or the olefinic hydrocarbon reactant, is depleted from the reaction media.

If desired, the reaction can be carried out in the presence of any suitable promoter, for example an organo derivative of a Group VA element defined by the following formula

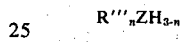

wherein each R''' is independently selected from the group consisting of aryl, alkaryl, cycloalkylaryl, araryl, aryloxy, alkaryloxy, arylaryloxy; wherein each R''' group contains from 6 to 12 carbon atoms; Z is selected from the group consisting of

As, Sb, or Bi; and n is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphosphine, tris(4-biphenyl)phosphine, tris(4-butylphenyl)phosphine, triphenylamine, diphenylamine, tris(3,5-dipropylphenyl)amine, triphenylarsine, tris(pentylphenyl)arsine, triphenylbismuthine, diphenylarsine, diphenyl-4-biphenylphosphine, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)phosphine, triphenylphosphite, diphenyl(p-tolyl)phosphine, triphenylphosphate, and the like, and mixtures thereof. The variant designated by n in mixtures of promoters represented by the formula $R'''_n ZH_{3-n}$ can vary, with the arithmetical sum of the value of n of individual promoters, from 2 to 3. The term "reaction promoting material" includes materials commonly called catalysts as well as materials commonly called promoters.

If employed, the amount of promoter utilized in the process of this invention can vary widely. In general, the mol ratio of promoter to unsaturated mononitrile reactant charged to the reaction zone would be in the range of about 1:20 to about 1:1. Preferably, the mol ratio of promoter to unsaturated mononitrile reactant charge would be in the range of about 1:10 to about 1:3.

The following example is presented in further illustration of the invention but should not be unduly construed in limitation thereof.

EXAMPLE

The following runs were conducted in a one liter reactor at 270° C for 2 hours. Following the designated reaction time, the reactor was cooled and vented. Fractional disillation of the liquid reaction mixtures and gas-liquid chromatographic analysis of resultant fractions gave the results tabulated in Table I.

In Runs 1 and 2 (first stage reaction) acrylonitrile and isobutylene are reacted in the absence or presence of water to form a mixture of olefinically unsaturated nitriles hereinafter called monoadduct (MA) containing predominantly 5-methyl-5-hexenenitrile with a small amount of 2,4-dimethyl-4-pentenenitrile.

In Runs 3 and 4 (second stage reaction) acrylonitrile and the monoadduct (MA) defined with respect to Runs 1 and 2 are reacted in the absence or presence of water to form a mixture of olefinically unsaturated dinitriles hereinafter called diadduct (DA) containing predominantly 5-methylene-1,9-nonanedinitrile and 5-methyl-4-nonenedinitrile with minor amounts of other isomers.

In Run 5 (single stage reaction) isobutylene, acrylonitrile, and the monoadduct (MA) defined with respect to Runs 1 and 2 are contacted to form the diadduct (DA) defined with respect to Runs 3 and 4.

Run 6 is in accordance with the present invention in which isobutylene, acrylonitrile, and said monoadduct (MA) are contacted in the presence of water to form predominantly said diadduct (DA).

run 5 consumed 0.41 gm less monoadduct (MA) per gam of acrylonitrile consumed than did the combination of runs 1 and 3 while producing 0.13 gm more diadduct (DA) per gram of acrylonitrile consumed.

The combination of run 2 (first state with water) and run 4 (second stage with water) is designated Determination III (two stage process with water). The algebraic difference between Determinations I and III is designated Improvement B, which represents the improvement achieved by the use of water in both stages of the two stage process. Specifically the two stage process utilizing water consumed 0.06 gm less monoadduct and produced 0.14 gm more diadduct than the two stage process which did not employ water.

On the basis of the use of the single stage process instead of the two stage process providing Improvement A and the use of water providing Improvement B, it could be predicted that the improvement achieved by the use of water in the single stage process over the two stage process without water would be the algebraic sum of Improvement A and Improvement B. This predicted value, which is designated Predicted Improvement C, indicates that it would be expected that the single stage process with water would consume 0.47 gm less monoadduct (i.e. no net consumption of monoadduct) while producing 0.27 gm more diadduct than the waterless two stage process.

However, the actual improvement achieved is far greater than Predicted Improvement D. Run 6 (single stage with water) is designated Determination IV. The

TABLE I

| Run | ACN$^a$ CHG$^b$ | ACN$^a$ REC$^c$ | ACN$^a$ CONV$^d$ | IB$^e$ CHG | MA CHG | MA REC | H$_2$O CHG | PRODUCTS$^f$ DA | PRODUCTS$^f$ HEAVIES | PRODUCTS$^f$ DIMER | POLYMER |
|---|---|---|---|---|---|---|---|---|---|---|---|
| 1 | 40 | 19.5 | 51.3% | 172 | 0 | 14.5 | 0 | 0.5 | 7.5 | ND$^g$ | 6 |
| 2 | 40 | 23.5 | 41.3% | 169 | 0 | 18.0 | 20 | 0.5 | 6.5 | 0.5 | 0 |
| 3 | 40 | 10 | 75.0% | 0 | 330 | 292 | 0 | 42.0 | 21.5 | 1.0 | 5 |
| 4 | 40 | 12.5 | 68.8% | 0 | 330 | 294 | 20 | 42.5 | 19.0 | 1.0 | 0 |
| 5 | 40 | 5.5 | 86.3% | 85 | 165 | 163 | 0 | 34.5 | 15.0 | 1.0 | 0 |
| 6 | 40 | 10.5 | 73.5% | 86 | 165 | 170 | 20 | 36.5 | 4.5 | 1.0 | 0 |

$^{(a)}$Acrylonitrile.
$^{(b)}$Grams charged to reactor.
$^{(c)}$Grams recovered from reaction mixture.
$^{(d)}$Conversion percent of acrylonitrile to products.
$^{(e)}$Isobutylene.
$^{(f)}$Grams of products recovered from reaction mixture.
$^{(g)}$Not determined.

Comparison of the above data are now presented on the basis of change in products per gram of acrylonitrile consumed. The combination of run 1 (first stage without water) and run 3 (second stage without water) is designated as Determination I (two stage process without water), while run 5 (single stage without water) is designated as Determination II. The algebraic difference between Determinations I and II is designated Improvement A, which shows that the single stage reaction without water is an improvement over the two stage reaction without water to the extent that algebraic difference between Determinations I and IV, which is designated the Actual Improvement D, shows that the single stage with water had a net production of 0.17 gm monoadduct, i.e. consumed 0.64 gm less monoadduct than the waterless two stage process, while producing 0.4 gm more diadduct than the waterless two stage process. Thus the Actual Improvement D exceeded the Predicted Improvement C by 0.17 gm monoadduct and 0.13 gm diadduct per gram of acrylonitrile consumed.

TABLE II

| Determination | | Runs | MA$^a$ | DA$^b$ |
|---|---|---|---|---|
| I | | 1+3 | −0.47 | 0.84 |
| II | | 5 | −0.06 | 0.97 |
| | Improvement A | | (0.41) | (0.13) |
| I | | 1+3 | −0.47 | 0.84 |
| III | | 2+4 | −0.41 | 0.98 |
| | Improvement B | | (0.06) | (0.14) |
| | Predicted Improvement C | (A+B) | (0.47) | (0.27) |
| I | | 1+3 | −0.47 | 0.84 |
| IV | | 6 | +0.17 | 1.24 |
| | Actual Improvement D | | (0.64) | (0.40) |

TABLE II-continued

| Determination | Runs | MA[a] | DA[b] |
|---|---|---|---|
| Increase of Actual over Predicted | | 0.17 | 0.13 |

[a] Grams monoadduct per gram of acrylonitrile consumed; − means net consumption of monoadduct; + means net production of monoadduct; ( ) means improvement over Determination I.
[b] Grams diadduct produced per gram of acrylonitrile consumed; ( ) means improvement over Determination I.

Reasonable variations and modifications are possible within the scope of the foregoing disclosure and the appended claims to the invention.

That which is claimed is:

1. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in the presence of an aqueous diluent, under reaction conditions suitable to produce at least one olefinically unsaturated dinitrile product, each of said olefinically unsaturated mononitrile reactant and said olefinically unsaturated mononitrile compound containing at least one hydrogen atom attached to a doubly bonded carbon atom and containing a cyano group attached to a carbon atom adjacent and doubly bonded to a carbon atom which is attached to at least one hydrogen atom, each of said olefinic hydrocarbon reactant and said olefinic hydrocarbon compound having at least one olefinic linkage having joined to one of the doubly bonded carbons a carbon atom having at least one hydrogen atom attached thereto, wherein during substantially the entire reaction period the concentration of said monoadduct reaction product in the resulting reaction mixture is within the range of about 10 to about 90 weight percent of the total reaction mixture.

2. A process in accordance with claim 1 wherein each of said at least one olefinic hydrocarbon reactant and said olefinic hydrocarbon compound is free of acetylenic unsaturation and has from 3 to 18 carbon atoms per molecule with from 1 to 2 ethylenically unsaturated, nonconjugated double bonds as the sole aliphatic unsaturation.

3. A process in accordance with claim 2 wherein each of said at least one olefinically unsaturated mononitrile reactant and said olefinically unsaturated mononitrile compound is free of acetylenic unsaturation, has from 1 to 2 ethylenically unsaturated, nonconjugated double bonds as the sole aliphatic unsaturation, and has from 3 to 18 carbon atoms per molecule.

4. A process in accordance with claim 3 wherein each of said at least one olefinic hydrocarbon reactant and said olefinic hydrocarbon compound is represented by the formula $R'_2C=CR'-CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound is represented by the formula RCH=CR—CN wherein each R is independently selected from the group consisting of hydrogen and hydrocarbyl radicals.

5. A process in accordance with claim 4 wherein said reaction conditions comprise a temperature in the range of about 100° C to about 500° C, a pressure in the range of about atmospheric to about 100,000 psig, and a mole ratio of said olefinically unsaturated mononitrile reactant to said olefinic hydrocarbon reactant in the range of about 10:1 to about 0.1:1.

6. A process in accordance with claim 4 wherein said reaction conditions comprise a temperature in the range of about 240° C to about 350° C, a pressure in the range of about 1000 to about 4000 psig, a contact time in the range of about 30 minutes to about 10 hours, and a mole ratio of said olefinically unsaturated mononitrile reactant to said olefinic hydrocarbon reactant in the range of about 5:1 to about 0.2:1; and wherein said at least one monoadduct reaction product comprises compounds having the structural formula

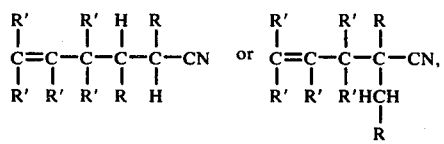

wherein R and R' are as defined above; and further comprising recovering from the resulting reaction effluent said at least one olefinically unsaturated dinitrile reaction product.

7. A process in accordance with claim 5 wherein said diluent consists essentially of water.

8. A process in accordance with claim 7 wherein during substantially the entire reaction period said concentration of monoadduct reaction product in said reaction mixture is maintained within the range of about 20 to about 80 weight percent.

9. A process in accordance with claim 8 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

10. A process in accordance with claim 1 wherein said reaction conditions comprise a temperature in the range of about 100° C to about 500° C, a pressure in the range of about atmospheric to about 100,000 psig, and a mole ratio of said olefinically unsaturated mononitrile reactant to said olefinic hydrocarbon reactant in the range of about 10:1 to about 0.1:1.

11. A process in accordance with claim 10 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

12. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in the presence of an aqueous diluent, under reaction conditions suitable to produce at least one olefinically unsaturated dinitrile product;

wherein each of said at least one olefinic hydrocarbon reactant and said olefinic hydrocarbon compound has from 3 to 18 carbon atoms and is represented by the formula $R'_2C=CR'-CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH=CR-CN$, wherein each R is independently selected from the group consisting of hydrogen and hydrocarbyl radicals;

wherein said at least one monoadduct reaction product comprises compounds having the structural formula

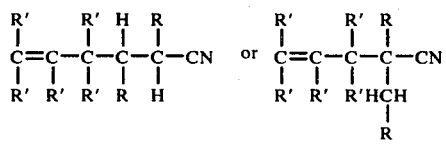

wherein R and R' are as defined above;

wherein said at least one olefinically unsaturated dinitrile product is formed by the monoaddition of a said olefinically unsaturated mononitrile reactant and a said monoadduct reaction product;

wherein said aqueous diluent comprises at least 50 weight percent water; the balance, if any, of said diluent being nonreactive with the reactants and the reaction products;

wherein the amount of said aqueous diluent is in the range of about 0.01 to about 40 parts by weight per part by weight of said at least one olefinically unsaturated mononitrile reactant;

wherein said reaction conditions comprise a temperature in the range of about 100° C to about 500° C, a pressure in the range of about atmospheric to about 100,000 psig, and a reaction time in the range of about two minutes to about 48 hours for a batch process or a liquid hourly space velocity in the range of about 0.05 to about 20 for a continuous process;

wherein the mol ratio of said at least one olefinically unsaturated mononitrile reactant to said at least one olefinic hydrocarbon reactant is in the range of about 10:1 to about 0.1:1; and wherein during substantially the entire reaction period the concentration of said monoadduct reaction product in the resulting reaction mixture is within the range of about 10 to about 90 weight percent of the total reaction mixture.

13. A process in accordance with claim 12 wherein said diluent comprises at least 80 weight percent water.

14. A process in accordance with claim 13 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

15. A process in accordance with claim 14 wherein said diluent consists essentially of water.

16. A process in accordance with claim 15 further comprising recovering from the resulting reaction effluent said at least one olefinically unsaturated dinitrile reaction product.

17. A process in accordance with claim 12 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

18. A process in accordance with claim 1 wherein said diluent consists essentially of water.

19. A process in accordance with claim 1 wherein each of said at least one olefinic hydrocarbon reactant and said olefinic hydrocarbon compound has from 3 to 18 carbon atoms and is represented by the formula $R'_2C=CR'-CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH=CR-CN$ wherein each R is independently selected from the group consisting of hydrogen and hydrocarbyl radicals.

20. A process in accordance with claim 19 wherein said reaction conditions comprise a temperature in the range of about 100° C to about 500° C, a pressure in the range of about atmospheric to about 100,000 psig, and a mole ratio of said olefinically unsaturated mononitrile reactant to said olefinic hydrocarbon reactant in the range of about 10:1 to about 0.1:1; and wherein said aqueous diluent comprises at least 50 weight percent water; the balance; if any, of said diluent being monoreactive with the reactants and the reaction products; the amount of said diluent being in the range of about 0.01 to about 40 parts by weight per part by weight of said at least one olefinically unsaturated mononitrile reactant.

* * * * *